United States Patent
Aggarwal (12)

(10) Patent No.: US 6,239,867 B1
(45) Date of Patent: May 29, 2001

(54) APPARATUS AND METHOD FOR GRADING, TESTING, AND IDENTIFYING GEMSTONES

(75) Inventor: Lalit K. Aggarwal, Philadelphia, PA (US)

(73) Assignee: Imagestatistics, Inc., Philadelphia, PA (US)

( * ) Notice: Subject to any disclaimer, the term of this patent is extended or adjusted under 35 U.S.C. 154(b) by 0 days.

(21) Appl. No.: 09/455,643

(22) Filed: Dec. 7, 1999

Related U.S. Application Data

(63) Continuation of application No. 09/085,797, filed on May 28, 1998, now Pat. No. 6,020,954.
(60) Provisional application No. 60/068,033, filed on Dec. 18, 1997.

(51) Int. Cl.[7] .................................................... G01N 21/00
(52) U.S. Cl. ............................................ 356/30; 356/425
(58) Field of Search ........................... 356/30, 425, 379, 356/445, 448, 72, 432, 348; 250/372; G01N 21/48

(56) References Cited

U.S. PATENT DOCUMENTS

| | | |
|---|---|---|
| 3,947,120 | 3/1976 | Bar-Issac et al. . |
| 4,012,141 | 3/1977 | Hanneman . |
| 4,049,350 | 9/1977 | Bruck . |
| 4,125,770 | 11/1978 | Lang . |
| 4,152,069 | 5/1979 | Bruck . |
| 4,162,125 | 7/1979 | Schmidt . |
| 4,162,126 | 7/1979 | Nakagawa et al. . |
| 4,291,975 | 9/1981 | Raccah . |
| 4,316,385 | 2/1982 | DeVries et al. . |
| 4,394,580 | 7/1983 | Gielisse . |
| 4,482,245 | 11/1984 | Makabe et al. . |
| 4,527,895 | 7/1985 | Rubin . |

(List continued on next page.)

FOREIGN PATENT DOCUMENTS 1547371   6/1979  (GB) .

OTHER PUBLICATIONS

Anderson, B.W., Gem Testing, Heywood & Company Ltd., 6th Ed. (1958).
Liddicoat, R.T., Handbook of Gem Identification, Gemological Institute of America (1966).
Matlins A. et al., Gem Identification Made Easy, Gemstone Press, Woodstock, Vermont (1994).
Russ, J.C., The Image Processing Handbook, 2nd Ed., CRC Press, Chicago (1995).
Theisen, V.P., Diamond Grading ABC, Rubin & Son, Belgium, 11th Ed. (1993).

*Primary Examiner*—Frank G. Font
*Assistant Examiner*—Layla G. Lauchman
(74) *Attorney, Agent, or Firm*—Dann, Dorfman, Herrell and Skillman, P.C.

(57) ABSTRACT

A method and associated apparatus for the standardized grading of gemstones is provided. The system gauges the spectral response of a gemstone subject to a plurality of incident light sources within an imaging apparatus. The operation of the imaging apparatus is controlled by an instruction set of a local station control data processor. Light energy data is captured in the form of pixel data sets via a charge coupled device of the imaging apparatus of the local station. The control data processor of the local station is operable linked to an analysis station, the station includes an analysis data processor and mass storage memory device. The memory device provides storage space for the instruction set of the analysis data processor as well as database records. The analysis station employs a data processor and model database for assessing the aesthetic and/or monetary value of gemstones by way of the communicated pixel data sets. Gemstones qualities are analyzed by the plurality of light sources of the imaging apparatus and quantified relative to model pixel data sets of the database and recorded for future reference therein.

52 Claims, 12 Drawing Sheets

U.S. PATENT DOCUMENTS

| | | |
|---|---|---|
| 4,529,305 | 7/1985 | Welford et al. . |
| 4,534,644 | 8/1985 | Beesley . |
| 4,647,194 | 3/1987 | Shigetomi et al. . |
| 4,693,377 | 9/1987 | Gerrard et al. . |
| 4,711,697 | 12/1987 | Kaukler . |
| 4,799,786 | 1/1989 | Gerrard . |
| 4,875,771 | 10/1989 | Bowley et al. . |
| 4,876,455 | 10/1989 | Sanderson et al. . |
| 4,900,147 | 2/1990 | Bowley et al. . |
| 4,907,875 | 3/1990 | Bowley et al. . |
| 4,951,825 | 8/1990 | Hawkins et al. . |
| 5,005,971 | 4/1991 | Davis . |
| 5,015,090 | 5/1991 | Welsman et al. . |
| 5,064,281 | 11/1991 | Davis . |
| 5,076,698 | 12/1991 | Smith et al. . |
| 5,077,475 | 12/1991 | Moriya et al. . |
| 5,118,181 | 6/1992 | Yifrach et al. . |
| 5,124,935 | 6/1992 | Wallner et al. . |
| 5,143,212 | 9/1992 | Roberts et al. . |
| 5,164,586 | 11/1992 | Hohberg et al. . |
| 5,196,966 | 3/1993 | Yamashita . |
| 5,237,407 | 8/1993 | Crezee et al. . |
| 5,239,354 | 8/1993 | Russell . |
| 5,260,763 | 11/1993 | Yamashita . |
| 5,317,390 | 5/1994 | Bolza-Schunemann et al. . |
| 5,379,102 | 1/1995 | Takeuchi . |
| 5,414,778 | 5/1995 | Schwartz et al. . |
| 5,459,313 | 10/1995 | Schrader et al. . |
| 5,512,999 | 4/1996 | Look et al. . |
| 5,544,254 | 8/1996 | Hartley et al. . |
| 5,559,436 | 9/1996 | Matthews et al. . |
| 5,615,005 | 3/1997 | Valente et al. . |
| 5,811,817 | 9/1998 | Ravich . |
| 6,020,954 * | 2/2000 | Aggarwal ............................... 356/30 |

* cited by examiner

APPARATUS AND METHOD FOR GRADING, TESTING, AND IDENTIFYING GEMSTONES

This application is a continuation of application Ser. No. 09/085,797, filed May 28, 1998, now U.S. Pat. No. 6,020,954. This application claim benefit to provisional application No. 60/068,033 Dec. 18, 1997.

BACKGROUND OF THE INVENTION

The monetary value of diamonds, pearls, and other precious gemstones can vary considerably relative to the aesthetic features of each stone. Such features, as, color, clarity, cut, shape, brilliance, etc., are important subjective determinants of value. For example, it is not uncommon to find gemstones of identical size and weight varying significantly due to the effect of such subjective determinants. As such, consistent measurement of these characteristics is a first step towards a reliable estimate of a gemstone's monetary value.

Presently, a variety of instruments are utilized to grade gemstones, such instruments include the simple eyeglass or loupe, as well as many sophisticated imaging instruments. Imaging instruments are commonly utilized in evaluating the objective and subjective qualities of gemstones, these instruments include simple ultra-violet lamps, microscopes, chelsea filters, calcite type dichroscopes, refractometers, polariscopes, spectroscopes, etc. Imaging instruments enable operators to visually analyze gemstones through illumination and magnification, or electronically gauge the gemstones refraction and/or reflection characteristics to incident light.

However, imaging instruments and systems are presently incapable of producing a reliable and reproducible index of a gemstone's objective and subjective qualities. The choice of imaging instrument, human judgement, and visual perception are all factors which impact the consistency of gemstone appraisals. Additionally, such appraisals have been heretofore incapable of measuring several subjective determinants such as brilliance, scintillation, polish, and cut quality.

For example, traditionally, the grading of a gemstone's color fails to consider the size of the gemstone, its transparency, flaws, degree of fluorescence, a lack of standard practice in preparation of a sample, and whether or not equivalent levels of illumination were utilized. A variety of instruments and methods for color grading rely on color comparison kits for visually comparing a sample, the kits are used to subjectively assign a color based on this comparison. Since it is well known that human judgment and eyesight vary from person to person, such color grading systems are unreliable. Some sophisticated instruments assign color by measuring light frequencies transmitted through or reflected from a surface, while others use reference light to evaluate shifts in color spectra and yet others convert the light frequencies into tri-stimulus which are used to assign a color to an object. Yet, fluorescence present in more than 50% of the diamonds and many other gemstones will shift color frequencies. Magnitude of UV radiation in a light source will therefore affect color grade. As can be appreciated, these devices have yet to achieve a level of consistency acceptable to the gain trade.

Moreover, these devices do not offer a system of assigning a cut grade to an object that matches any one of the several well known round and fancy gemstone cuts. Cut analysis can be improved by direct measurements of the side, top, and bottom views of objects being analyzed. Based on these measurements, Proportions of objects can be measured and they can be assigned a shape, a cut grade, and sorted. The foregoing devices are incapable of precisely obtaining with certainty the minimum and maximum dimensions of a gemstone, such as girdle or table measurements.

Similarly, the clarity of a diamond and other transparent gemstones is based on the number, size, and distribution of flaws, inclusions, bubbles, crystals, and any other foreign matter than will distract from its internal flawless beauty. Surface defects in the form of scratches, bruting marks, naturals, and feather are also important to the quality of a gemstone. A process for automatically identifying location, size and type of internal flaws in gem stones has yet to be developed.

Additionally, such subjective determinants as brilliancy and scintillation in certain gem stones is highly prized. Naturally, inconsistent lighting conditions will produce different brilliancy readings. While a lighting standard must be developed to obtain consistent results, it should be flexible enough to allow for differences in gemstones, presently, inconsistent brilliancy and scintillation valuation of gemstones is commonplace.

Such inconsistencies in evaluating the above objective and subjective gemstone properties has encouraged the proliferation of sophisticated counterfeiting and synthetic gemstone industries which further obfuscate the gemstone appraised process. Identification or authentication of these objects is a primary component of a reliable gem appraisal practice. As sophisticated counterfeiting procedures are developed to alter appearance such as laser drilling, radiation, and the substitution of with highly reflective plastics and liquids, ever more reliable equipment and procedures are necessary to separate natural goods from those which have been altered, enhanced or those that are man made. Furthermore, there is well established need in the jewelry trade to fingerprint gemstones for future identification. Gemstones removed for cleaning or sold on consignment may be switched. Insurers and consumers are interested in reclaiming lost or stolen goods recovered by police or retailers. A method is needed that will accurately measure and automatically record many attributes of a gemstones which can be used hierarchically to match a gemstone.

In addition to the aforementioned security concerns, presently, gemstones must be shipped or sent by a courier for appraisal or for evaluation by an interested buyer. This activity is time consuming, expensive, and places inventory at risk. An electronic means of transferring text, numerical and visual data that accurately represents the various attributes of a gemstone can significantly improve transactions while reducing associated shipping, insurance and security costs. This functionality requires not only communication capability but a database capability that can automate recording of text, audio and video information from gem analysis. The database must be secure and fully integrate inventory functions with analysis, management, retailing, and marketing of gem stones and information.

The apparatus in accordance with the present invention, provides a reliable and reproducible evaluation, measurement, and recording system for quantifying heretofore objective and subjective gemstone characteristics.

SUMMARY OF THE INVENTION

A method and associated apparatus for the standardized grading of gemstones is provided in which the spectral response of a gemstone subject to a plurality of incident light sources is captured via a charge coupled device (CCD). An imaging apparatus employing a CCD camera is operably linked with an analysis station, the analysis station including a data processor and database for processing the spectral response data as captured by the CCD camera in the form of pixel data sets. The database employs a library of exemplary gemstone pixel data sets as measured by the apparatus, the library data functioning to relate, compare, and distinguish the spectral response of an individual gemstone's pixel data set to the reference pixel data sets of the database. The data processor of the analysis station provides an instruction set for facilitating communication with the imaging apparatus, analyzing communicated pixel sets, and producing reports to, identify the gemstone's shape, quantify, and reliably grade heretofore subjective qualities of gemstones. The reports are communicated from the analysis station to the imaging apparatus for reproduction by an operably linked local printer.

The data processor of the analysis station communicates with a control data processor of the imaging apparatus. The control data processor of the apparatus provides an instruction set for automating the steps necessary to precisely position and operate the imaging hardware. The control data processor has local and wide area communication capability for communicating captured pixel data sets to the analysis station in addition to the hardware positioning/actuation analysis instruction set.

An object of the invention is to extract consistently and accurately, size, shape, and proportion information from the side, top, and bottom images of a gemstone using the data processing instruction set. This information is used for cut analysis, weight calculation, and for assigning a cut grade using a statistical procedure such as a cluster or linear discriminant analysis. Cut grade analysis is based on cut grade standards for different types of cuts and the respective proportions of various dimensions of a gemstone, diamonds in particular.

Still another object of the invention is to measure color and assign a color grade to a gemstone. This is accomplished by using an illuminant standard such as D 55 recommended by the C.I.E. (International Commission on Illumination) having a color rendition and an ultra violet component that closely resembles North-Daylight. A database of these readings is developed for stones of different but known colors along with the size, cut, fluorescence and flaw information for each stone. This multivariate data is used to assign a color grade using a statistical procedure such as cluster or linear discriminant analysis.

Yet another object of the invention is to identify, delineate, and measure flaws and assign a clarity grade to a gemstone. This is accomplished by immersing a gemstone in refractive index liquid, illuminating the stone from the bottom/sides, and imaging it from the top. Additional illumination from the top, front, and side is obtained and a stone is rotated to obtain the best image of internal flaws, inclusions etc. The captured image is analyzed by a data processor to delineate and measure any features. The size and the location of the features relative to the size of the gemstone and its cut is used to assign a clarity grade.

Still another object of the invention is to check for fluorescence, its intensity as well as the characteristics of the radiation emitted as a result of ultra violet simulation; This is accomplished by taking two images. A stone that fluoresces will yield a first R.G.B. reading (red, green, blue) when illuminated by ultra violet radiation and a second R.G.B. reading with the ultra violet source disabled. The variations in the two readings are used to measure the degree of fluorescence, the color of visible emission spectra, and a fluorescence grade is assigned based on this information. This imaging process eliminates the need for an expensive color camera sensitive to low level radiation or integrating an image over time.

A further object of the invention is to measure brilance and scintillation of a gemstone. Images are taken from the table side of a gemstone. After adjusting for the intensity of illuminant, an average of total illumination over the face of a gemstone issued to measure brilliancy. Images used for brilliancy measurement are also used to measure scintillation. This is accomplished by thresholding a gray scale image and measuring pixels above a certain minimum level to be determined by trade for different gemstones. The ratio of total pixels exceeding the defined threshold and the area of the face of a stone in pixels is used to calculate the scintillation of the gemstone.

Another objective of the invention is to measure reflectance from the table of the gemstone, identify surface scratches and describe the shape and size of the table. For clear stones, a collimated light illuminates the table of a stone at an angle; image of the surface reflectance is captured and processed. A ratio of the average reflected light to the average value of the illuminant measures reflectance. Thresholding is used to identify surface scratches which can be automatically measured by the number of pixels. A morphological image algorithm is used to determine the shape and size of the table.

A further objective of the invention is to authenticate a gemstone. Each stone is identified by the quantified properties as determined by the imaging apparatus, and those values are utilized to identify it. The system is designed to evaluate multiple properties of a gemstone for authentication. Calculated weight from the apparatus can be compared to scale weight and refractive index of a stone can be calculated. Internal features of a stone can be mapped, described and used in authentication, presence or absence of fluorescence, its intensity and frequency can be calculated, and surface features and textures as described above can be extracted from an image. Filters such as: Chelsea, Waltonhodgkinson-Hanneman, frequency, and polarization filters are placed in the path of light between an object being analyzed and a lens to separate stimulants and synthetics from natural stones.

Yet another object of the invention is to provide a database for storing text, video, graphic, and audio data corresponding to a plurality of gemstones. Furthermore, the database is capable of automated search, report generation, automatic input and output of data from other machines and from the analytical component of the invention. The database is remotely located from the apparatus to ensure the security of its contents.

Another object of the invention is to have secure local and wide area communication capability to transfer text, video, graphic and audio data. This capability is used for centralized data processing and to monitor the performance of remotely distributed devices.

BRIEF DESCRIPTION OF THE DRAWINGS

The foregoing summary, as well as the following detailed description of the preferred embodiments of the present invention, will be better understood when read in conjunction with the accompanying drawings in which.

DETAILED DESCRIPTION OF THE PREFERRED EMBODIMENT

Figure 1:
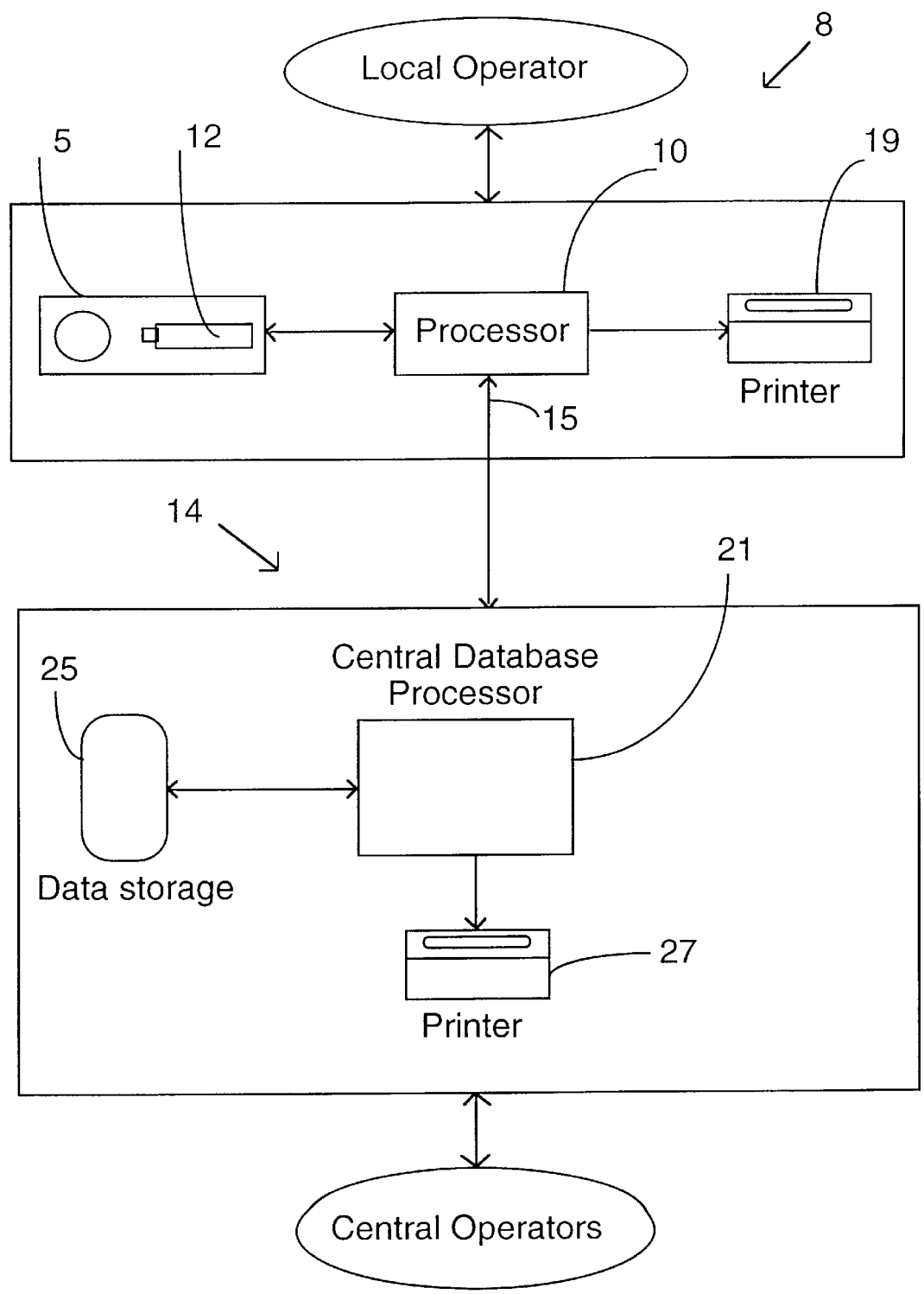
FIG. 1 shows a functional block diagram of the gemstone grading system in accordance with the present invention.

An automated gemstone grading and data management system is provided wherein the aesthetic and/or monetary value of a gemstone is determined relative to the measured spectral response of light energy incident to a gemstone. Gemstones are illuminated by a plurality of light sources such that the spectral response of the gemstone is captured as a pixel data set, gauged, quantified and recorded for future reference via a CCD camera of an imaging apparatus.

More particularly, the present invention provides a local imaging station for the automated valuation of gemstones. The local imaging station is operably linked to an analysis station for communicating captured incident light data sets thereto. The analysis station employs a data processor and model database for assessing the aesthetic and/or monetary value of gemstones by way of the communicated pixel data sets. Gemstones are subject to a plurality of incident light sources of the imaging apparatus. The spectral response of a gemstone to the incident light sources is quantified relative to model pixel data sets of the database and recorded for future reference therein.

The method and associated apparatus for the standardized grading of gemstones, gauges the spectral response of a gemstone subject to a plurality of incident light sources of the imaging apparatus. Incident light energy is captured via the charge coupled device of the imaging apparatus of the local station. The operation of the imaging apparatus is controlled by a local station control data processor and instruction set. The control data processor of the local station is operably linked to an analysis station, the station includes an analysis data processor and mass storage memory device. The memory device provides storage space for the instruction set of the analysis data processor as well as database records.

The data processor of the analysis station provides an instruction set for facilitating communication with the imaging apparatus, analyzing communicated pixel sets, and producing reports of the analysis function. The instruction set includes analytical and statistical image models which extract pertinent objective aesthetic and value attribute indicia from the pixel data sets. The reference value database serves as a model of exemplary gemstone pixel data sets as detected by the imaging apparatus. The database provides a reference for comparing incident light data communicated to the analysis station, the model data functioning to relate, compare, and distinguish the spectral response of a gemstone having unknown quality subjected to the illumination protocol of the imaging apparatus. Additionally, the analysis station includes a mass storage memory devices for storing the reference value database, analysis instruction set, and report information which may include text as well as visual and audio data. The reports are communicated from the remotely located analysis station to the imaging apparatus by way of a telecommunication network such as a LAN (Local Area Network) or WAN (Wide Area Network) for reproduction at the local station via an attached printer.

The local station includes the imaging apparatus, control processor, and printer. The control data processor of the local station provides an instruction set for automating the steps necessary for the precision positioning and actuation of the components necessary to operate the imaging apparatus. The data processor has local and wide area communication capability for communicating with the data processor of the analysis station via a communication port. A preferred embodiment of the system and methods in accordance with the present invention will now be described with reference to the enumerated drawing figures.

Referring now to FIG. 1, the system includes a local station 8 which is operably linked by way of a telecommunication network 15 to an analysis station 14. The local station 8 includes an electronic imaging apparatus, generally designated 5, for imaging a gemstone such as a diamond or pearl. Local station 8 also includes a control data processor 10 for controlling the operation of the imaging apparatus 5 by way of a programmed instruction set, and a printer 19. The data processor function is preferably performed by a general purpose computer, such as a personal computer, including a microprocessor for the processing of the imaging apparatus instruction set. The control data processor 10 of local station 8 is programmed with one or more suitable network protocols to permit it to capture and communicate pixel data sets to the analysis station 14 with which it is operably linked.

In the preferred embodiment, the general purpose computer includes volatile RAM (Random Access Memory) and non-volatile ROM (Read Only Memory) for facilitating the use of known computer operating environments such as the Windows operating interface. The general purpose computer may additionally employ a data management software program to catalog, format and update communicated reports communicated from the analysis station 14. The interface software enables the visual display of data set reports and appraisals communicated from the analysis station 14, as well as the manual entry of information to the reports via the data management software. A printer 19 is provided at the local station 8 for generating reports communicated from analysis station 14.

Imaging apparatus 5 of local station 8 includes a (CCD) charge coupled device 12 for capturing and communicating pixel data sets to the data processor 10. The pixel data sets captured by the processing of gemstone 7 within apparatus 5 provide incident light data to the analysis station 14. The control data processor 10 of local station 8 communicates the captured pixel data sets to the remotely located analysis station 14.

The analysis station 14 includes a data processor 21, nonvolatile memory device 25, and printer 27. Analysis station 14 is operably linked by way of a telecommunication network 15 to local station 8. The data processor 21 or analysis station 14 operates the analysis and database instruction set for storing, comparing, and analyzing captured data sets. The database of analysis station 14 can be remotely queried or updated utilizing the software of the local station data processor 10. A printer 27 is provided at analysis station 14 for generating activity reports, appraisal reports, and the like.

The data processor function of the analysis station 14 is preferably performed by a general purpose computer, such as a personal computer or main frame computer, including a microprocessor for the processing of the analysis and database instruction set. The analysis station computer is programmed with one or more suitable network protocols to permit it to obtain pixel data sets from the local station 8 with which it is connected. In the preferred embodiment, the general purpose computer of analysis station 14 includes volatile RAM (Random Access Memory) and non-volatile ROM (Read Only Memory) for facilitating the use of known computer operating environments such as the Windows operating interface in addition to mass storage device 25 provided for the storage of generated analysis reports. The processed image data sets enable reliable appraisal of the gemstones in addition to verifying the authenticity and quality of each gemstone. The analysis station may similarly employ data management software and encode network communications with the appropriate application and network layer protocols to facilitate known electronic commerce standards. The memory device 25 of analysis station 14 may include volatile as well as non-volatile forms of computer memory. Preferably, the database is stored in a non-volatile mass storage device such as a hard disk drive. Copies of data set reports and appraisals may be transported via portable memory mediums such as floppy disks, CD roms, DAT's, etc. or communicated to a local station 8 or other remote backup sites over the telecommunication network.

In an alternative embodiment, the data processor function 10 of the local station 8 may be integrated with the imaging apparatus 5 such that a stand alone imaging and control apparatus is provided. The stand alone unit functions to combine the general purpose personal computer with that of the imaging apparatus 5 such that an on board dedicated data processor would be provided for communicating with remotely located analysis station 14 and controlling the operation of apparatus 5.

IMAGING APPARATUS

Figure 2:
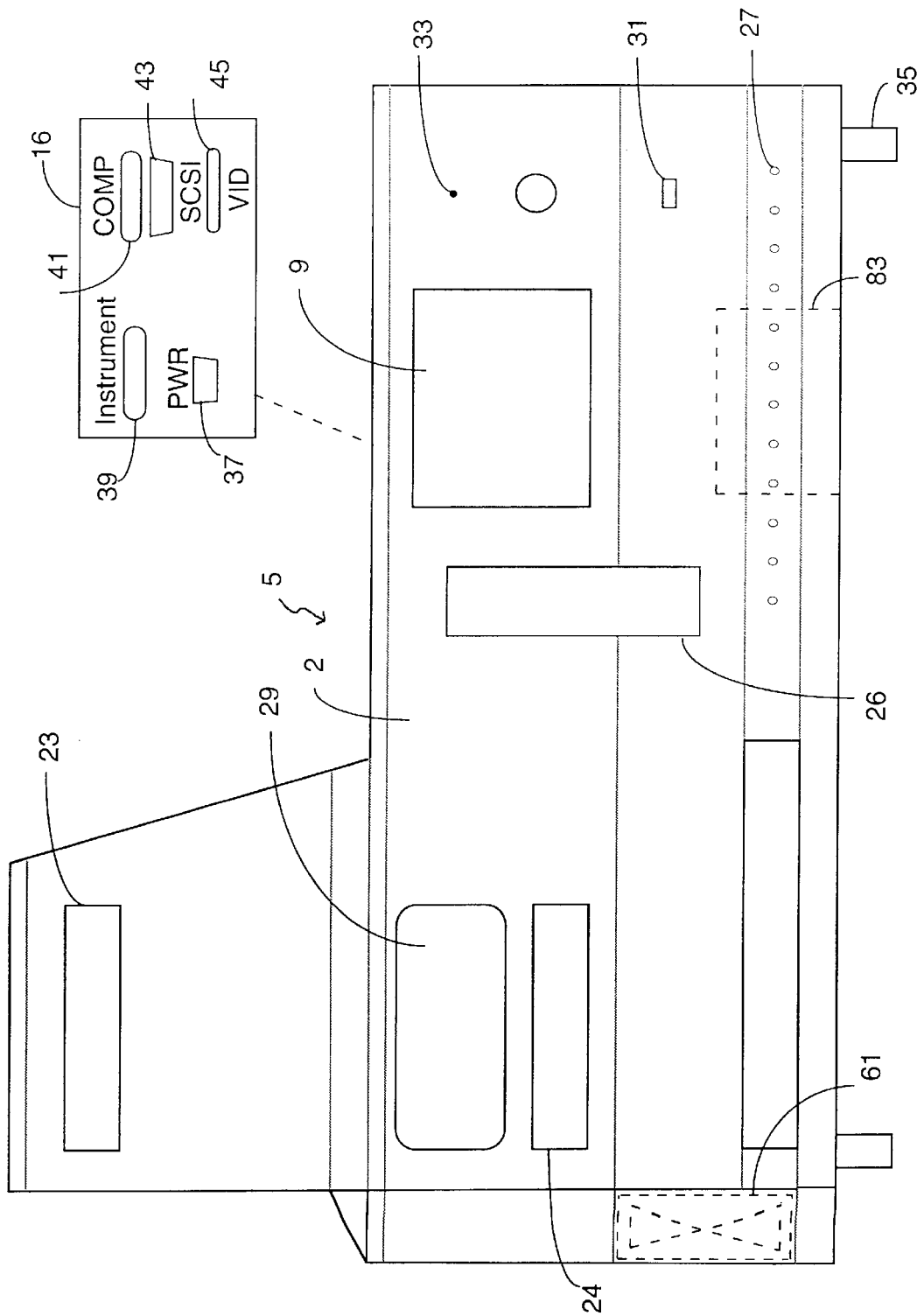
FIG. 2 shows a front view of the imaging apparatus of the gemstone grading system shown in FIG. 1.

Referring now to FIG. 2, imaging apparatus 5 is shown. The imaging apparatus 5 includes housing 2, display 9, status lights 27, access door 29, filter arrays 23, 24, and 26, power switch 31, legs 35a–d, power indicator 33 and output port 16. The entire apparatus 5 is enclosed by the housing 2; the housing 2 can be easily removed for access to the inside of the apparatus 5. Either plastic or metal may be used for the construction of the housing. The housing seals the interior of the apparatus 5 from external light sources. The interior surfaces of the housing are coated with a non-reflective light absorbing material to limit reflection of the plurality of lighting elements housed therein. Four leveling legs 35a–d with shock absorbing pads are used to level the device and reduce vibrations. The imaging apparatus 5 employs fan 61 and 83 to blow air into the imaging apparatus through air filters to facilitate air circulation such that dust does not enter and settle into the apparatus 5, the air circulation also ensures that the ambient temperature does not exceed operating parameters.

Display 9 is preferably an LCD (Liquid Crystal Display) which provides a visual representation of the placement of a gemstone 7 within imaging apparatus 5 such that the gemstone may be optimally located on a device platform. In a preferred embodiment, the LCD 9 displays instructions from the computer and the images of a stone being analyzed. However, in an alternative embodiment a monitor of an operably linked personal computer can perform this function. The status light 27 are an array of LED's (Light Emitting Diodes) each one of which correspond to an operation of the imaging apparatus. The illumination of the appropriate LED indicating the actuation of the corresponding apparatus function such that monitoring troubleshooting is facilitated without removing the housing 2 of the imaging apparatus 5.

The imaging apparatus 5 is supplied by 120 VAC 60 HZ power supply controlled by a toggle switch 31. The power switch 31 connects the apparatus 5 with a power source, and LED indicator light 33 is enabled upon powering the apparatus 5 by way of switch 31.

Access door 29 slidably engages the housing 2, providing access to the interior of imaging apparatus 5 for the placement of a gemstone therein. Filter arrays 23, 24 and 26 slidably engage the imaging apparatus at locations designed to position the filter elements to block light energy of a preselected frequency from being captured by the internal CCD device of the imaging apparatus.

Output port 16 includes an AC power supply connector 37, an RS-232 INSTRUMENT port 39, DB 25 COMP control port 41, video port 45, and SCSI port 43.

The AC power supply connector is attached to a power source for powering the electrical components of the apparatus 5. The COMP port controls the actuation to different electrical devices as dictated by the instruction set of the data processor 10 of the local station 8. The INSTRUMENT port provides an auxiliary connection for use with additional gemstone grading instrumentation. Video port 45 transmits pixel data sets from CCD camera 12 of the apparatus 5 to the data processor 10 of local station 8. SCSI port 43 is provided for the connection of computer peripherals such as a local hard disk or zip drive to the apparatus 5.

Figure 3:
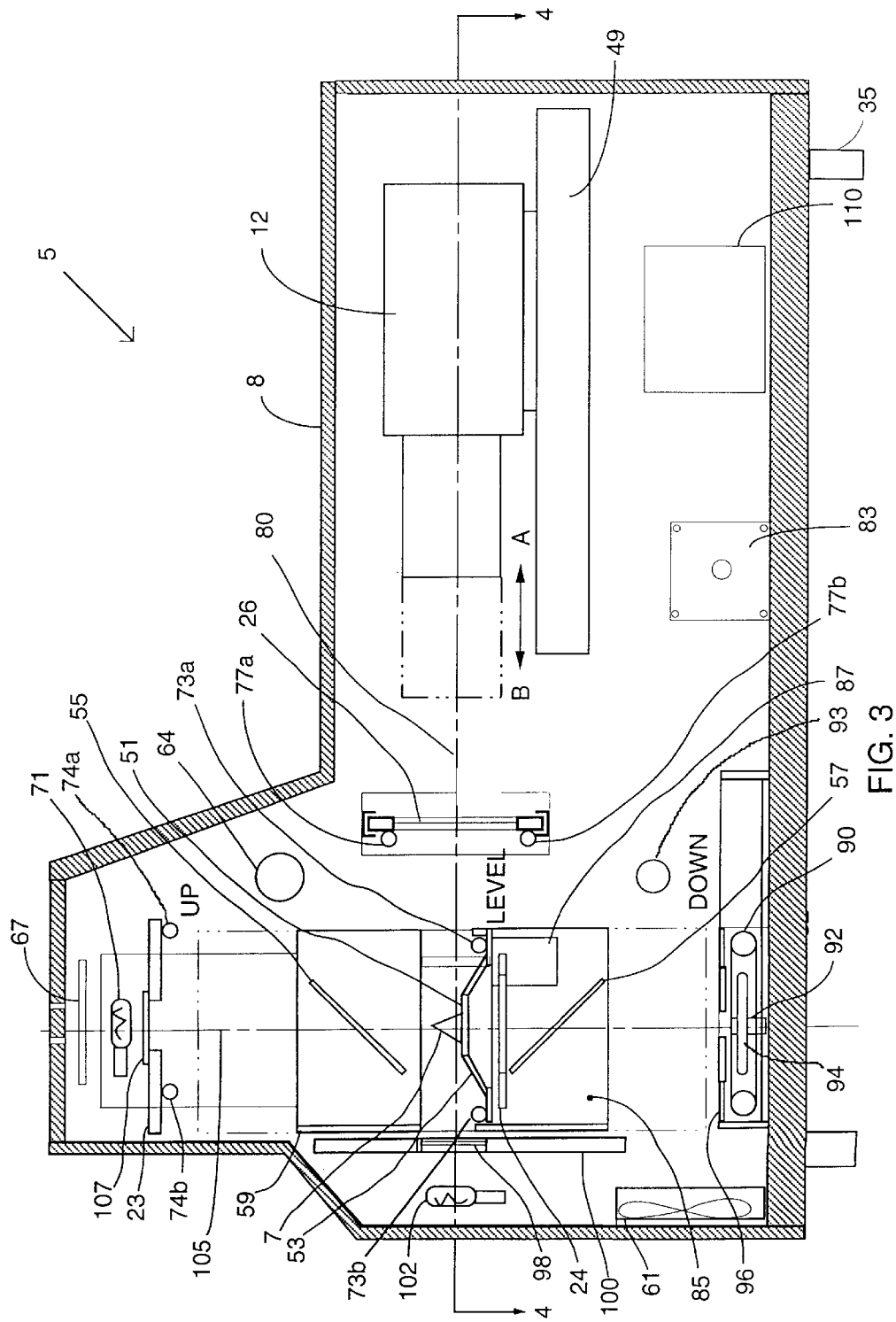
FIG. 3 shows a front sectional view of the interior of the imaging apparatus of the gemstone grading system shown in FIG. 1.

Referring now to FIG. 3, a side sectional view of the imaging apparatus 5 is shown. The imaging apparatus 5 of the local station provides pixel data sets for transmission to analysis station 14. The data sets are communicated in a graphic file format such as TIFF or JPG. The pixel data sets are incident light images captured by a charge coupled device 12 of imaging apparatus 5, such as manufactured by JVC model #TK107OU and an appropriate lens attached thereto. The pixel data sets of light energy incident to the gemstone 7 are processed by analysis station 14 to analyze these images and extract pertinent information therefrom to produce an appraisal report on the gemstone 7.

Forward of the lens of CCD 12 is a filter assembly 26 capable of holding multiple filters used to block light of a desired spectrum. For example, infrared and ultra violet filters are used to block infrared and ultra violet light frequencies. Such filters are critical to color and fluorescent analysis as infra red and ultra violet light are invisible to the human eye but affect reading taken by the CCD camera 12.

For example, a diffraction grating may be used to obtain a spectrum of light transmitted through or reflected from a gemstone 7 for use in the identification of stimulants; Similarly, a chelsea filter may be utilized to identify emeralds.

The filter assembly 26 has a ring light 77 to illuminate a stone from a first direction. Light source 77 is used to detect surface scratches, facet structures, and to perform color analysis of dark stones. An ultra violet light 64, capable of short, long wave, or black UV illumination is provided for fluorescent analysis useful in identifying a gemstone 7, detecting treatments, measuring fluorescence, and distinguishing stimulants from natural gemstones.

IMAGING PLATFORM

Figure 4:
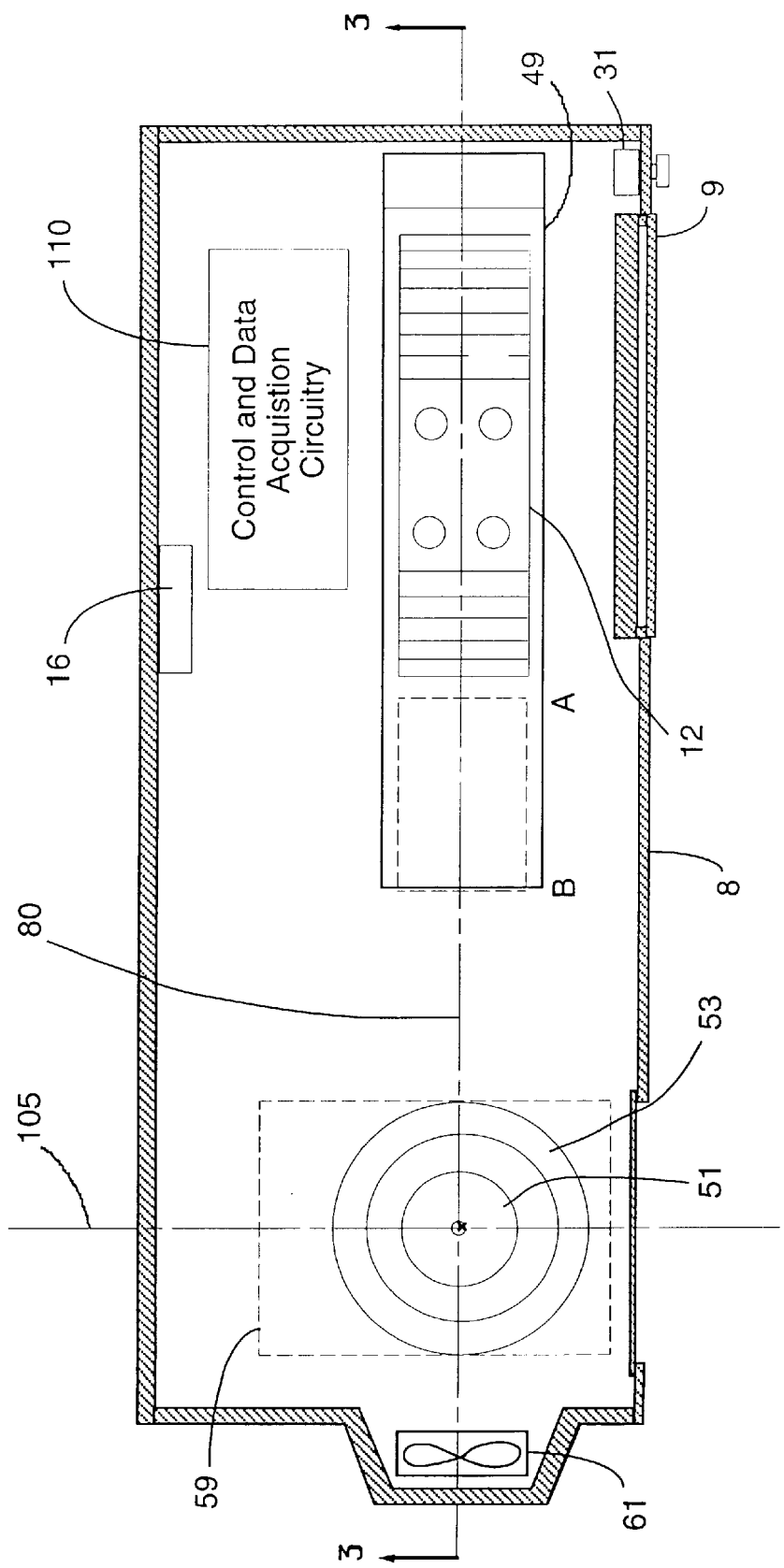
FIG. 4 shows a top view of the imaging apparatus of the gemstone grading system shown in FIG. 1.

Referring more particularly to FIGS. 3–4, the CCD camera 12 is positioned to travel between a first location A and a second location B. The points A and B correspond to a first and second positions of a linear positioner 49 which travels along a focal axis 80 (i.e., the x-axis). The linear positioner 49 is driven by servo motor 86 of the control circuitry 110 (shown in FIG. 6). The linear positioner is actuated to move the camera 12 between point A and B as dictated by the data processor 10 of local station 8. The instruction set of the data processor dictates the actuation of the linear positioner 49 to compensate for the vertical movement of the gemstone 7 away from the local axis. The distance between positions A and B is preselected to correspond to the vertical travel distance of the gemstone when positioned above or below the focal axis 80. Thus, the camera is refocused on the gemstone image by varying its horizontal location, however it should be recognized that a camera having an automated lens assembly operably linked to the data processor 10 of local station 8 is within the scope of the invention. The linear positioner 49 obviates the need for cost prohibitive auto focus systems.

GEMSTONE STAGE

A unitary stage 59 travels along a processing axis 105 through three positions, namely UP, LEVEL, and DOWN. The unitary stage is partially shielded by a stage baffle 85. The stage baffle 85 is a partial rectangular enclosure spanning the vertical length halfway between the LEVEL and DOWN and UP positions of the processing axis 105. The baffle 85 obstructs light reflectance while passing light along a particular angle of incidence. The baffle enclosure has openings at the ends perpendicular to the processing axis to permit light entry to the enclosure from the top and bottom light sources. Similarly, the enclosure has its camera facing surfaces removed to permit light data to pass to the camera 12 at any of the three stage locations. In the LEVEL position, the enclosure surface facing access door 29 is open to permit insertion of a gemstone 7, as well as the surface facing light source 102.

The unitary stage 59 includes light directing means' 55 and 57, motorized Y-axis linear positioner 87 actuated by servo motor 83 of circuitry 110, rotatable platform 53, translucent platform portion 51, and stage light 73. The positions of the unitary stage 59, are defined by the alignment of the platform 53 along y-axis positions UP, LEVEL, and DOWN, with the focal axis 80; The LEVEL position defined as being aligned with the focal axis 80. Light directing means' 55 and 57 are provided to direct images of gemstones 7 to camera 12 when the platform 53 is positioned above or below the focal axis 80. The light directing means' 55 and 57 may be specially oriented beam splitters, lenses and/or reflective mirrors. In the preferred embodiment, the light directing means' 55 and 57 are a combination beam splitter and mirror. The light directing means' include a mirror and beam splitting portion on its facing surface such that either method can be selected for directing images to camera 7.

A stone to be analyzed is placed within the stage 59 with its table side facing platform 53. The vertical movement of the stage along the processing axis 105, between the UP, LEVEL, and DOWN positions, is enabled by the motorized Y-axis linear positioner 87. The preferred embodiment of the stage makes it feasible to obtain images of the front, back, top, and bottom of the gemstone 7 from a plurality of light sources and locations. The stage has a rotatable platform 53 rotated by a servo motor 120 of circuitry 110. The platform 53 rotates at predetermined intervals to facilitate imaging of the entire gemstone surface area. The center of the rotatable platform 53 has a transparent window 51 on which the gemstone 7 is placed. The transparent window 51, having a transparent surface area boundaries designed to circumscribe the periphery of the gemstone 7 placed thereon. A holding device may be required to maintain the placement of mounted stones and to hold a stone in place when the rotatable platform 53 is rotated at high speeds. The platform is circumscribed by a stage light 73. The stage light 73 can be a ring light or array of light emitting diodes to illuminate the undersides of a gemstone 7.

Positioned below the rotatable platform 53 is a second filter assembly 24 with an iris for regulating the light traveling to the transparent window 51 of the rotatable platform 53 from below. Additionally, the assembly accommodates filters and or masks used in refractive index and flaw analysis imaging methods. Positioned below the filter assembly 24 is a light directing means 57 mounted at a 45° angle to the horizontal, traveling through the center point of the light directing means is processing axis 105 which is aligned with the center point of the transparent window 51.

When the unitary stage 53 is in the LEVEL position, light data along the focal axis 80 incident to gemstone 7 is captured by CCD camera 12.

When the unitary stage 59 is moved to the UP position and the center point of the light directing means 57 is aligned with that of the focal axis 80, light is directed by the means 57 along focal axis 80 and into the lens of camera 12. This arrangement allows a view of the bottom or the table side of a gemstone 7.

A light directing means 55 is positioned above the platform at a 45° to the horizontal with its center point along processing axis 105. This configuration allows light from the stone side of the window 51 to illuminate a gemstone 7. The reflected light of light directing means 55 is redirected to the lens of camera 12 when the stage is moved to the DOWN setting, the center point the light detecting means 55 is aligned with that of the focal axis 80; This arrangement allows a top view of the stone. When the stage 59 is in its normal position, and by rotating the platform 53, multiple images of the profile, front and back of the gemstone 7 can be taken.

Opposite the camera side of the stage 59, a diffused light source 102 provides back lighting used in profiling the silhouette of a gemstone 7, used to extract coordinate values from the corners of a gemstone 7 when imaging the periphery. For, example a side image is captured with the stage in the LEVEL position, the top and bottom perspectives obtained in the DOWN and UP positions of stage 59 respectively via light directing means 55 and 57.

Figure 5:
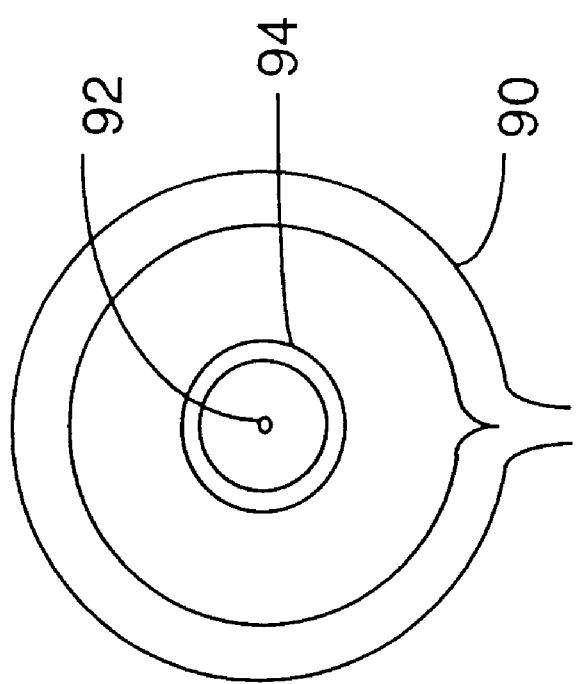
FIG. 5 shows a top view of the bottom light assembly of the imaging apparatus of the gemstone grading system shown in FIG. 1.

Referring more particularly to FIG. 5, a bottom light assembly includes ring light 90, bottom light 94 and laser light 92. The ring light 90 is a D 55 ring light having a color rendition and an ultra violet component that closely resembles North-Daylight at 5500° K. The circular configuration ensuring consistent application of the light to the periphery of the gemstone 7. The ring light 90 is used in color, brilliancy and scintillation analysis and placed in such a manner relative to the stone as to create dark field illumination, (i.e., creating a dark background with respect to the gemstone 7 from the camera perspective). The bottom light 94 can be any dimmable and diffusible light source, in the preferred embodiment it is a halogen light. Bottom light 94 and light 93 are used in clarity analysis. Diffused light 93 is placed off to the side of the processing axis 105 and is used in conjunction with light 94 to get a reflection of the table with the camera 12. Additionally, bottom light 94 and light 93 are used in capturing the morphology of the table of a gemstone 7 for cut analysis, the table image is also utilized to accurately measure the polish of the table, its surface characteristics, and match a gemstone 7 through its unique sequence or side images. The laser light 92 is used to align a gemstone 7 on the glass window via LCD display 9, obtain laser scatter, and to measure refraction.

Above the stage 59 is light source 74 to provide direct lighting of the gemstone 7 useful in observing its top portion. Light source 74 can be any dimmable diffused light. In the preferred embodiment a halogen or LED light source 74 is utilized. Light 74 is used in clarity analysis, surface defect detection, culet analysis, color analysis of dark stones and pearls and lustre in pearls. Above the light 74 is another filter assembly 23 that can hold a diffuser and one or more filters for blocking light of a preselected frequency. Above the filter assembly 23 is a light source 71 used to profile the girdle, match and calculate the perimeter of the gemstone 7, measure the total surface area, and is used in clarity analysis. Right above the halogen light 71 is a canopy (not shown) that lets warm air out without letting outside light to penetrate the inside of the apparatus 5.

CONTROL CIRCUIT

Figure 6:
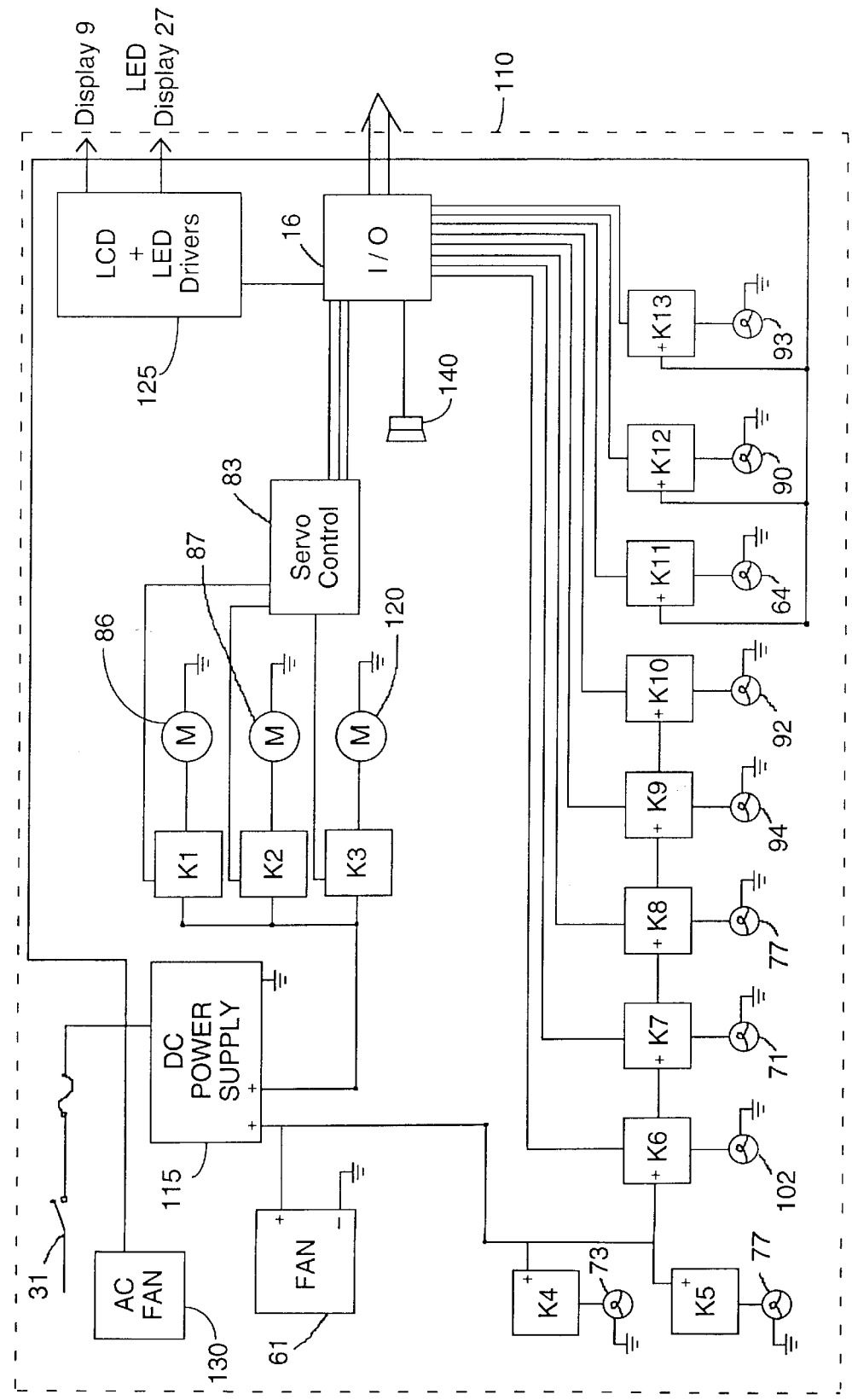
FIG. 6 is a schematic diagram of the electrical control circuit of the imaging apparatus shown in FIG. 1.

Referring now to FIG. 6, control and data acquisition circuit 110 dictates the actuation of the internal motors and light sources of apparatus 5. A DC power supply rectifies the AC line current provided through switch 31, for components of control and data acquisition circuit 110 which require DC power. Control and data acquisition circuit 110 includes relays K1–K13, servo controller 83, servo motors 86, 87, and 120, LCD and LED driving circuitry 125, speaker 140, DC fan 61, and AC fan 130.

The relays K1–K13 are selectively actuated to enable the lamp or motor connected thereto by way of data port 16. The servo motors are driven by servo control unit 83. The actuation of motors and lamps is provided by the data processor 15 of local station 8 through an interface of data port 16, preferably the DB-25 COMP port 41. For example, upon reception of an actuation signal from the data processor 15 for light source 102 of apparatus 5, the data port 16 triggers relay K6 to enable light source 102.

Speaker 140 provides audible indicia of the execution of instruction by apparatus 5. The audible indicia may be prerecorded descriptive phrases such as "color", "clarity", and "scintillation".

IMAGING METHODS (LEVEL)

Figure 7:
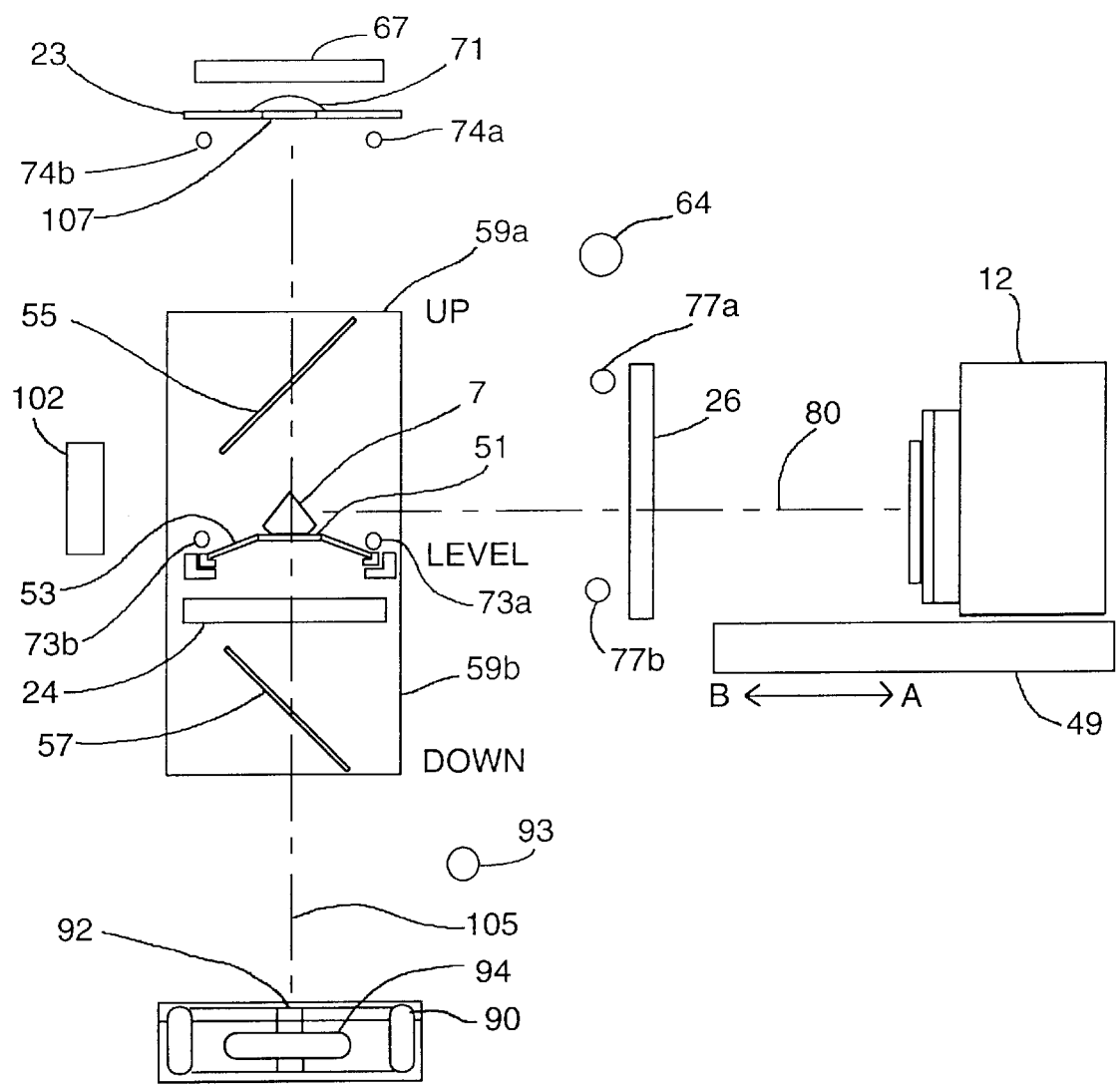
FIG. 7 is a side view of the imaging apparatus in a first imaging position.

Referring now to FIG. 7, a first image capture configuration is shown for capturing a first set of images, namely, images A1–A19. It should be noted however, that the image capture procedure, lamp and motor actuation sequence can be altered or truncated to accommodate specific gemstones 7 such as pearls which may not possess the full range of qualities such as table dimensions, clarity, brilliance etc.

The lights and motors of apparatus 5 are controlled by local station 8, specifically apparatus 5 is controlled way of the instruction set of the data processor 15 of local station 8. The preferred sequence and duration of light and/or motor actuator will now be described herein for analyzing a diamond gemstone 7.

At start up, the apparatus 5 is initialized by closing power switch 31. A diagnostic analysis of the lights and motors of apparatus 5 is completed by the data processor 15 of local station 8 including the calibration of dimmable lights to desirable intensities, upon satisfaction of this test, indicating all devices as functioning, an instruction set sequence is shown on LCD display 9 or monitor (not shown).

At start up, the laser light 92 is enabled such that a beam of visible light is aligned with processing axis 105 to facilitate the placement of a gemstone 7 on rotable platform 53. Unitary stage 59 is initialized in the LEVEL position to align rotatable platform 53 with focal axis 80. The camera 12 is set to the "A" position along focal axis 80 position by x-axis linear positioner 49.

A gemstone 7 is prepared for analysis, a cleaning fluid such as alcohol is applied to the gemstone 7 to remove particles and impurities which may interfere with the imaging process. Sliding door 29 of apparatus 5 is opened and a gemstone 7 is placed at the center of the translucent window 51 of platform 53 with the guidance of laser light 92 directed therethrough, sliding door 29 is closed and the gemstone 7 is in position for analysis by apparatus 5.

Imaging begins by disabling laser light 92. A profile image of the gemstone 7 (A1) is obtained by enabling D55 light 90 and light 102, rotatable platform 53 is rotated to obtain the profile of bezel facets and image (A1) is captured by camera 12 of apparatus 5. The profile image (A1) is communicated from apparatus 5 to the data processor 15 of local station 8 for further processing by analysis station 14.

A second image (A2) is obtained for color analysis by disabling light 102, light 90 remains enabled. The resulting image of gemstone 7 is captured with camera 12. Similarly, the second image (A2) is forwarded for further processing to analysis station 14. The process of obtaining profile and color images (A1) and (A2) is repeated dependent of the cut of the diamond as determined by the data processor 10 of local station 8.

For example a third image is obtained by rotating the platform 53 by a preset amount, the degree of rotation determined by the instruction set of the data processor 15, enabling light 102, light 90 remains enabled and another image of the profile (A3) is captured by camera 12.

Similarly, a fourth image (A4) is taken by again disabling light 102, light 90 remains enabled and the image is captured by camera 12 for color analysis.

For a round brilliant cut diamond the first and second images (A1, A2) are captured from eight locations determined by the preselected rotation of platform 53 resulting in sixteen separate profile and color images (A1–A16). These images are used in cut analysis and for color measurement.

Upon completion of the profile and color imaging, light 102 is disabled and fluorescent light 64 is enabled to obtain a fluorescence image A17 which is used together with the last captured color and profile image of set (A1–A16) to check for fluorescence levels, these images may range from (A1) and (A2) to (A15) and (A16) depending on the cut of the diamond. As can be appreciated image (A17) is taken only for those gemstones with fluorescent qualities.

Image (A18) is captured by disabling all lights, and enabling front light 77 to image the front of a gemstone 7, image (A18) is captured by camera 12. The platform 53 is rotated 180° and another image (A19) is captured. Images (A18) and (A19) are used to gauge external surface flaws on the sides of a diamond, faceting and the quality of the girdle.

I. STAGE UP

Figure 9:
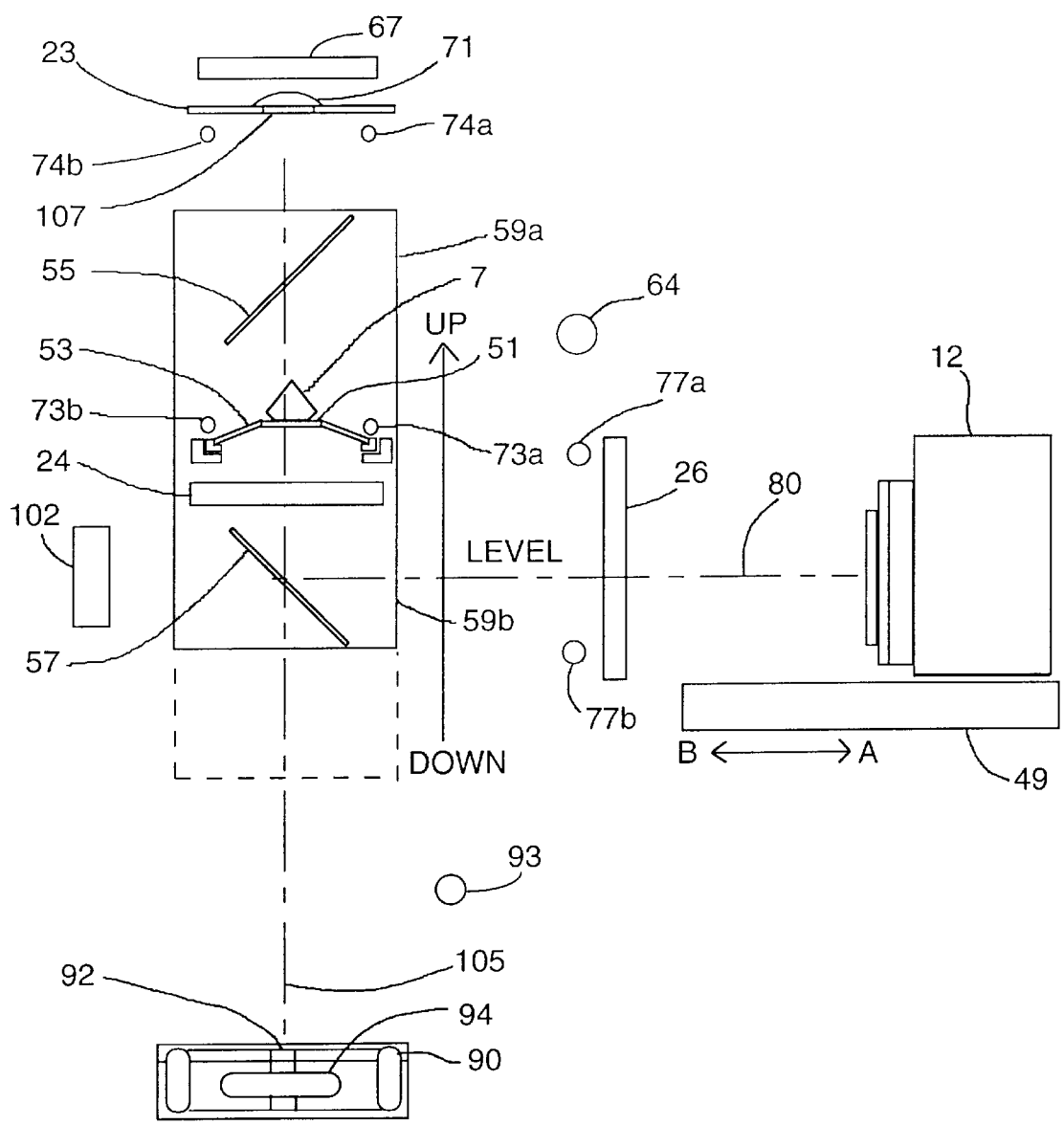
FIG. 9 is a side view of the imaging apparatus in a third imaging position.

Referring now to FIG. 9, a second image capture configuration is shown for capturing a second set of images, namely, images A21–A24. The second stage setting is accomplished by moving the stage 59 up along processing axis 105 by way of y-axis linear positioner 87. Stage 59 is moved up such that the center of light directing means 57 is aligned with focal axis 80 and platform 53 is in the UP position. The camera 12 is moved from position "A" to position "B" along focal axis 80 by the linear positioner 49.

Brilliance and scintillation image (A21) is obtained by enabling D55 Light 90. Image (A21) used for brilliance, scintillation and matching analysis is captured by camera 12.

Girdle image (A22) is captured by camera 12 by disabling Light 90 and enabling light 71 to capture an image (A22) for girdle measurements.

Table and luster image (A23) is captured by camera 12 by disabling light 71 and enabling light 92 and 93 are enabled. Image (A23) is captured for use in luster analysis and to determine the shape and size of the table for cut and matching analysis.

Laser scatter image (A24) is captured by camera 12 by disabling lights 92 and 93 and enabling laser light 94 to capture the internal laser scatter in image (A24). This is done to replicate the image capture used by Gem Print, a proprietary system, for extending support services and is not essential to this invention. Gem Print uses the laser scatter pattern to match gemstone 7 to stones in an existing pixel data base. All lights are disabled prior to the initiation of the third state setting.

II. STAGE DOWN

Figure 8:
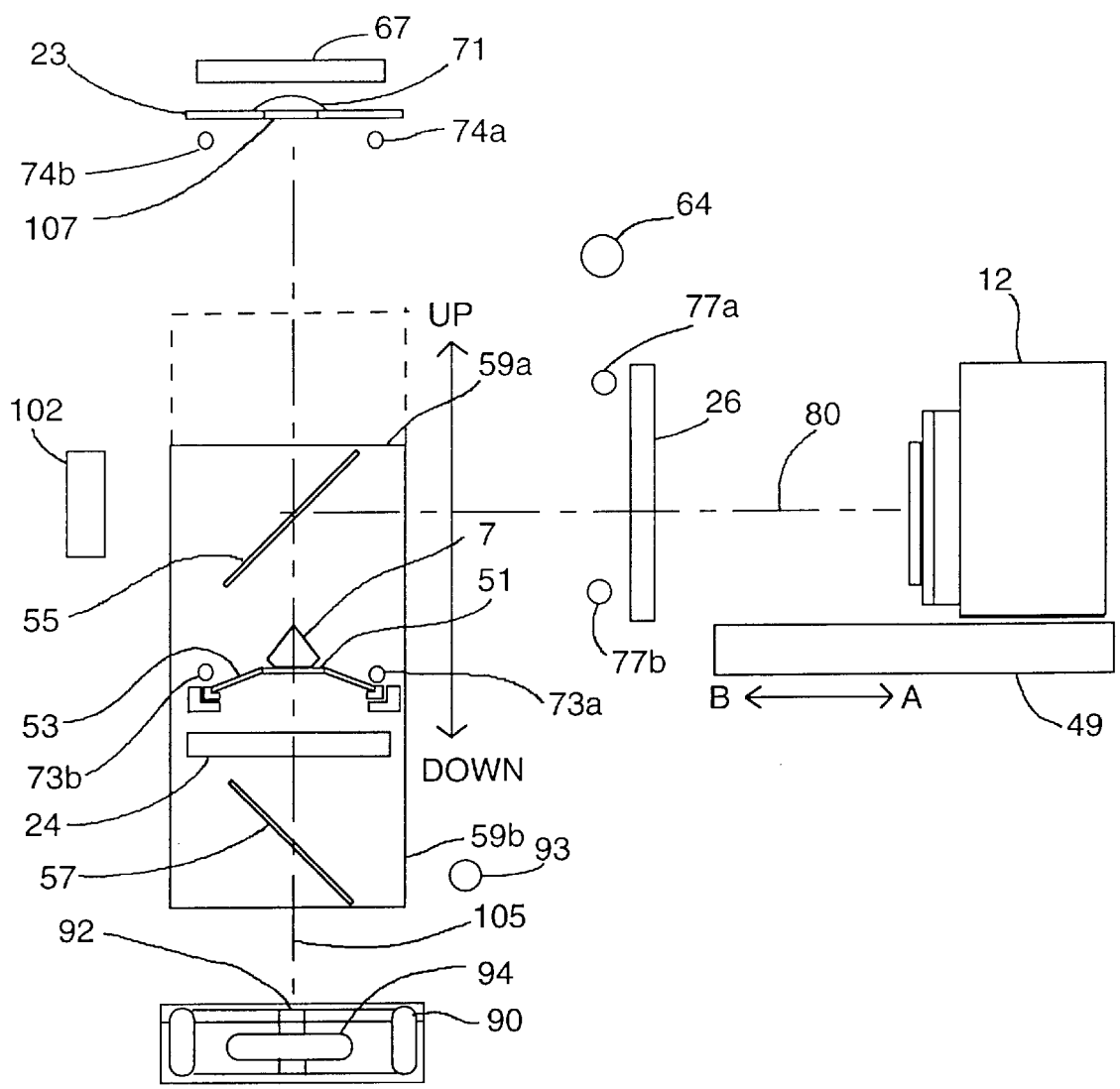
FIG. 8 is a side view of the imaging apparatus in a second imaging position.

Referring now to FIG. 8, a third image capture configuration is shown for capturing a third set of images, namely, images (A25 and A26). In the third stage setting stage 59 is moved down along processing axis 105 by way of y-axis linear positioner 87. The stage 59 is moved down such that the center of light directing means 55 is aligned with focal axis 80 and platform 53 is in the DOWN position. The camera 12 remains in position "B" along the focal axis. A combination of lights, namely 74, 71 and 73 are turned on to get the best image (A25) which is used to examine the culet, table facets and surface features. At this point the gemstone 7 is removed from the platform 53, all lights are disabled.

FLAW ANALYSIS/MATCHING

Prior to flaw analysis, gemstone 7 is removed from the apparatus 5 and thoroughly cleaned. For flaw analysis, image (A26), one of two preferred procedures may be used. In the first procedure, a gemstone 7 is placed on a glass plate with its underside etched to diffuse light, a small amount of high viscosity immersion oil is dispensed at the center of the plate and a gemstone 7 is placed on the plate in contact with the oil. The plate is placed above the translucent window 51 and lights 92, 93 and 73 are turned on to capture image (A26) for internal flaw analysis.

Another approach is to totally immerse a diamond in a small crucible with a diffused base and walls. The crucible is placed on platform 53 for capturing image (A26) with camera 12. This method yields a slightly better image quality. For small flaws, 5 microns or larger, the lens of camera 12 is set to higher magnification and multiple images may be taken by scanning the gemstone 7.

This completes a step by step procedure for capturing images used in the grading of a diamond. It should be clear that apparatus 5 can be used to obtain other images from the setup described above.

SOFTWARE PROCESSING

Figure 10:
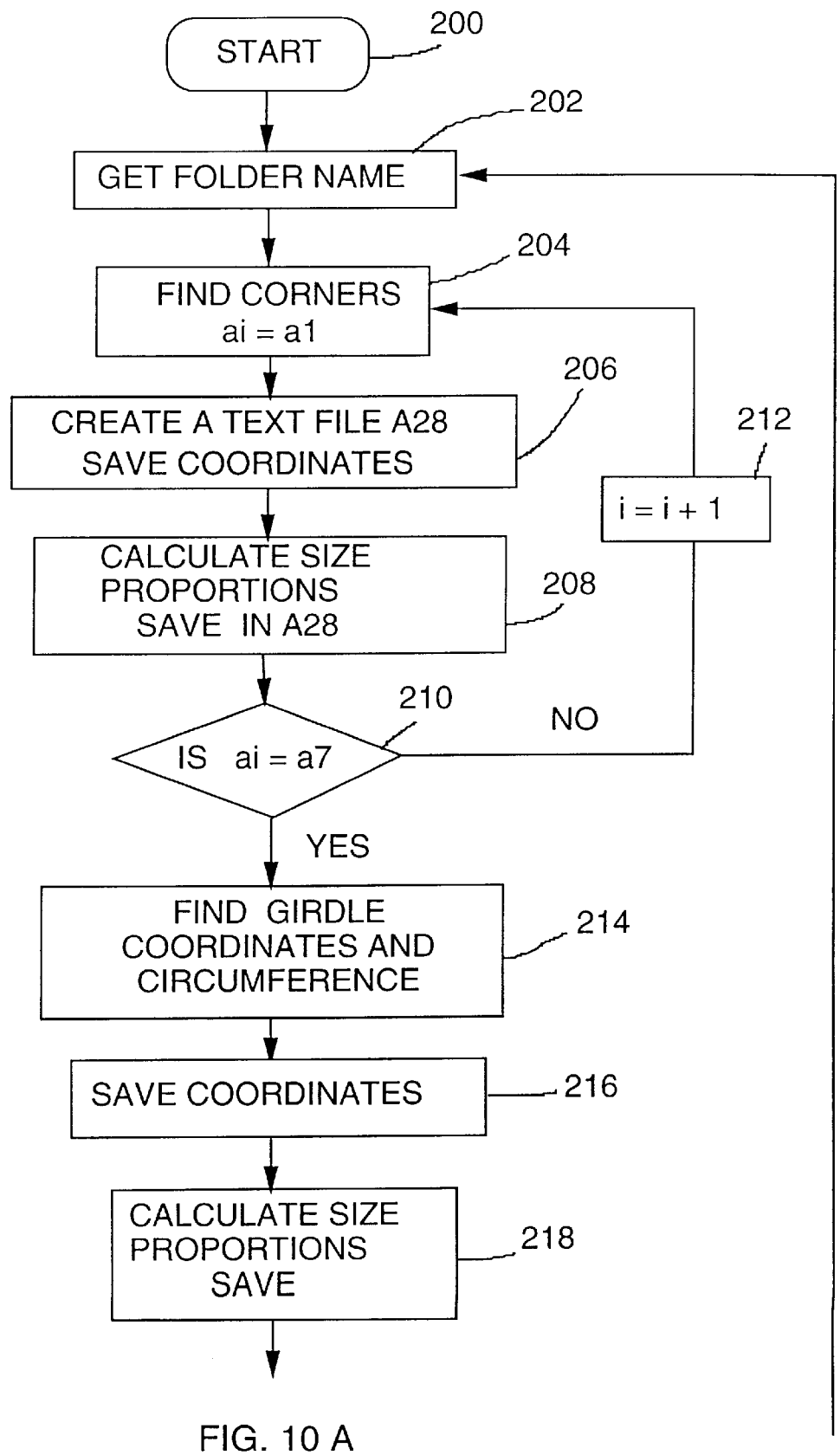
FIG. 10A is a logical flow diagram of the cut analysis method of operating the imaging apparatus of FIG. 1.
FIG. 10B is a continuation of the logical flow diagram of FIG. 10 showing the color analysis method of operating the imaging apparatus of FIG. 1.
FIG. 10C, is a continuation of the logical flow digram of FIG. 10 the brilliance, scintillation, flaw and polish analysis method of operating the imaging apparatus of FIG. 1.
Figure 10:
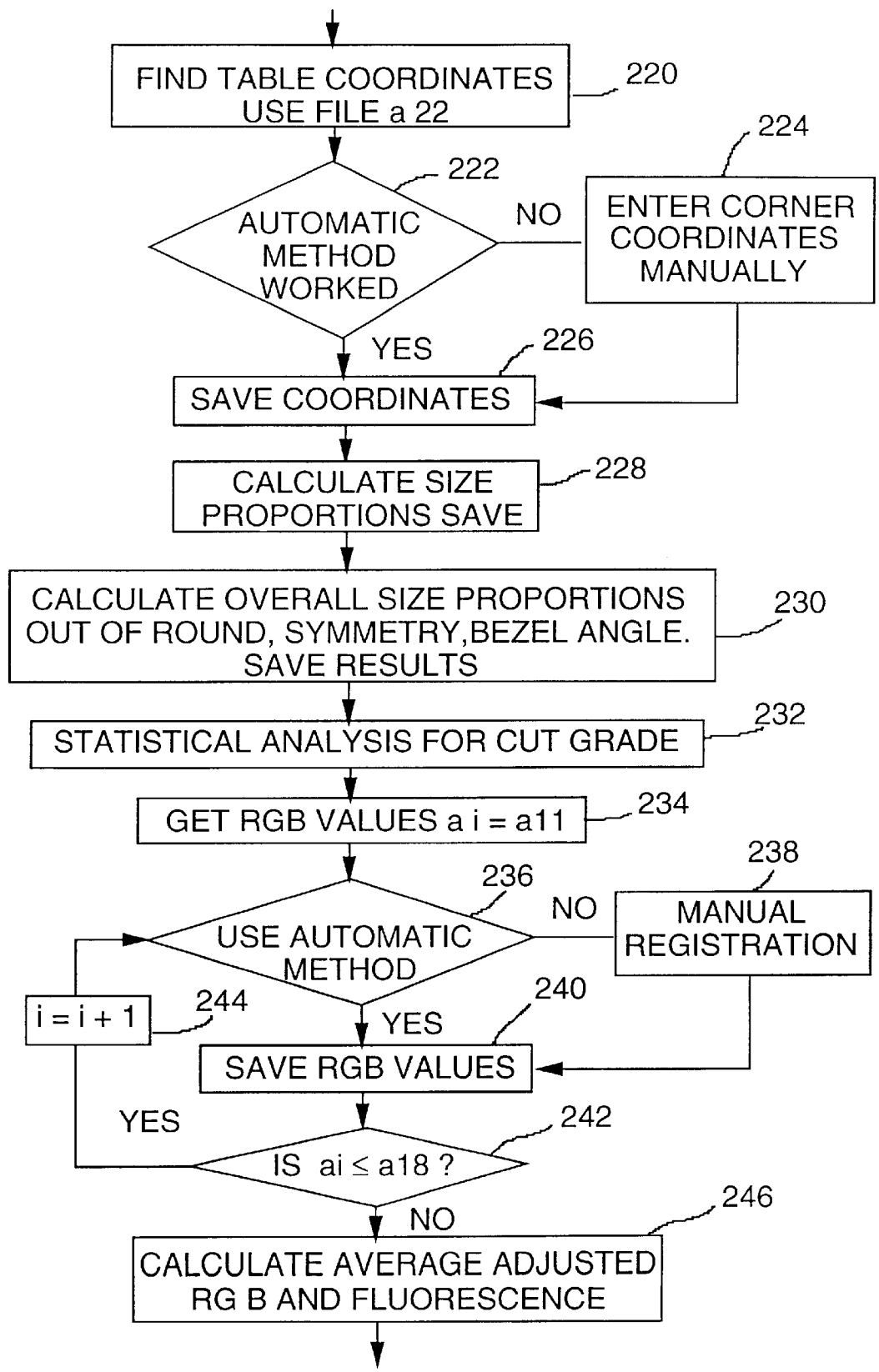
Figure 10:
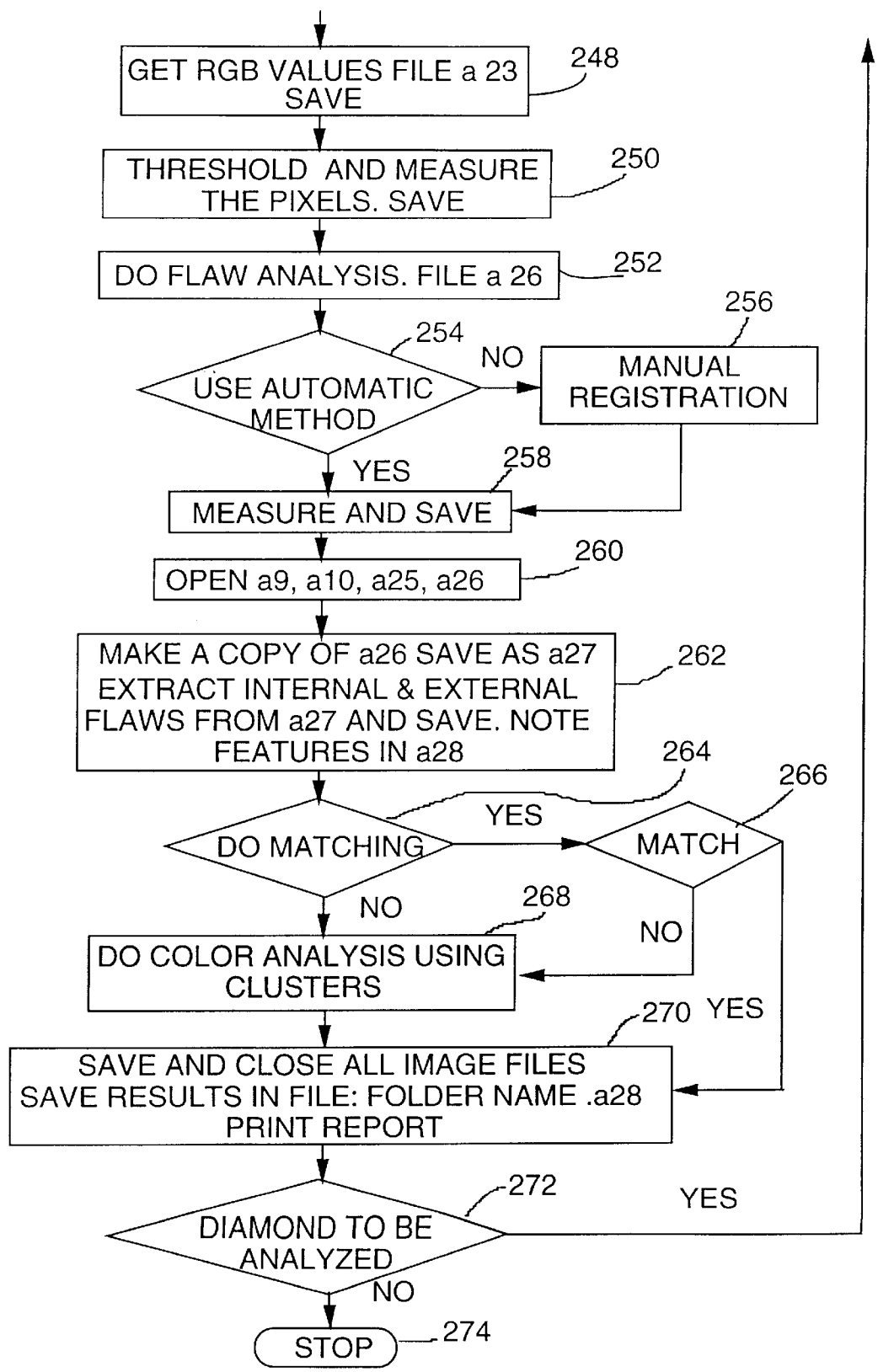

Referring now to FIGS. 10A–10C, there is shown an example of the procedure by which the images captured by imaging apparatus are obtained and organized, and more particularly, the manner in which incident light data is utilized in the grading and identification of gemstones. A start-up, step 200, the processing parameters, constants, and counters of local processor 10 are initialized and the lighting elements of the imaging apparatus are calibrated to ensure consistency in lighting levels. Each gemstone analyzed by the apparatus produces a set of pixel data images in accordance with the invention. The images for each gemstone analyzed are stored in a unique analysis folder in the memory of local station 8. The folder organizes the pixel data images into files as captured by the apparatus 5 along with a text file that contains information on ownership, eventual results of the analysis, an appraisal report and other pertinent information. The text files may be created in part by manually entered information via an appropriate user interface of apparatus 5.

Image data in the file folder of local station 8 is analyzed by the data processor 21 of the analysis station 14. In the preferred embodiment, the file folder or set of image and text files are sent to the analysis station 14 for processing and compilation in the analysis station database. The folder and its contents are backed up for data security, thereafter, contents of the folder are analyzed to prepare an appraisal report based on the communicated pixel images of analyzed gemstones.

Referring now to FIG. 10A, in step 202 the local station 8 creates the unique file folder for the storing of gemstone appraisal data. The illustrative procedures described herein utilize diamond gemstones. Beginning with step 204, the cut of the gemstone is determined by defining points about the gemstone periphery. The profile of a diamond is a convex set of pixels of low gray scale values against a background of pixels lighter in color. A change from a light to a darker pixel identifies a pixel to be on the boundary. Knowledge of the shape of a diamond is utilized with the pixel gray scale values to identify corner points. Thus, in diamond analysis for example, the points define the maximum dimension of the table, girdle and culet. The value of pixels per millimeter (mm) is known and carats per cubic millimeter is assigned interactively and is roughly 0.00173801. As such, the dimension of the gemstone is determined by the processor 10 of local station 8 by performing of plurality of geometric calculations based on the defined constants and obtained gemstone coordinates. Proceeding to step 206, the first cut analysis extracts coordinate data for the corners via the profile image (A1). The gemstone size coordinates are stored within a file of the folder. Next, in step 208 the gemstone size proportions are determined by geometric calculations utilizing the obtained coordinate points. A counter, steps 210 and 212, repeats this process for obtaining images necessary to analyze fancy cut gemstones, up to a maximum of eight for round fancy cut stones. The process is repeated until all profile images are processed.

The cut analysis continues in step 214 by defining maximum girdle point about the gemstone periphery, the coordinates are saved in step 216, and girdle size and perimeter are calculated in step 218.

Referring now to FIG. 10B, the final cut analysis includes step 220 for defining table coordinates. Since the morphology of the table of the round brilliant cut generally follows an octagonal shape, a morphological algorithm is employed to find the corner points. For certain fancy cuts and where necessary, a cursor is used to manually mask the corner points of a table. Step 222 permits the operator to enter this data manually via step 224. The table coordinates are stored within a file of the folder stored within the memory of local station 8. The coordinate data is further analyzed as outlined flowchart in steps 230 and 232 to calculate the girdle size, table width, table height, culet height, pavilion angle, table angle, girdle thickness and various ratios associated with cut analysis and gemstone appraisal practices known to those skilled in the art. Cluster analysis is then used to assign a cut grade based on certain proportional attributes. A database including diamonds of different proportions and associated cut grades are used in cluster analysis. The cluster analysis assigns a cut grade based on the proximity of a gemstone to a cut grade in multidimensional space.

Gemstone color analysis begins with step 234 and is done by obtaining average R.G.B. (red, green, blue) values from color images (A2, A3, A6 . . . ) in the image pixel region delineated by the girdle and the table facets, by sampling the color of a smaller region a more predictable and accurate color reading is obtained. Steps 236 and 238 provide the option of manually entering the R.G.B. values. The R.G.B. image sets are stored within a file of the gemstone analysis folder, step 240. The number of R.G.B. images taken is determined by a counter in steps 242 and 244.

Diffraction of light caused by such gemstones as diamonds skews the R.G.B. color reading by misrepresenting the body color of the gemstone. Furthermore, the diffraction of the light energy into spectral components increases a standard error in the R.G.B. average. The software of the data processor 21 of analysis station 14 compensates for this by removing outlier value images from the statistical analysis. Thereafter, an average of the R.G.B. pixel intensity values is calculated in step 246.

Referring now to FIG. 10C, average R.G.B. values are additionally obtained from the gemstone color image under ultra violet radiation via step 248, image (A17). The difference between the average R.G.B. value without ultra violet radiation and under ultra violet radiation are used to determine the presence of fluorescence in step 250. Fluorescence devalues diamonds. This analysis is done using a statistical model. Likewise, R.G.B. values from the color images are transformed to C.I.E., L.A.B., and L.U.V. coordinates. Before assigning a color grade, flaw analysis is performed in step 252. Flaw identification may be performed manually as illustrated by steps 254 and 256.

A processing algorithm is used for flaw analysis. A combination of thresholding and filters is used to highlight internal flaws, inclusions, pin points etc. The size and location of these flaws is measured. Internal flaws are identified by the algorithm and saved in a file (A27). A clarity grade is assigned based on the size of the flaws compared to the overall area of the face of a stone weighted by its location; flaws near and within the boundaries of a table diminish the value more than flaws that are farther away from the surface and closer to the girdle area. Proceeding to step 258 the flaw data is stored within a file of the analysis folder. Flaws are identified and marked and a gemstone image file (A28) is created in step 262. Images (A9), (A10), (A25), and (A26) are analyzed in step 260 for determining gemstone brilliance, scintillation, and polish analysis. This approach is taken to get as much information as possible to ascertain if the system has analyzed the same gemstone.

To do brilliancy analysis, average R.G.B. values are extracted from the brilliancy image using a processing algorithm. C.I.E., standard L.A.B., and L.U.V. tri-stimulus coordinates are calculated adjusting for incident light intensity. A ratio of the average gray value and a standard is used to calculate brilliancy. Scintillation is measured by first thresholding the image and then calculating the total number of pixels that have an average gray scale value above the threshold level. A ratio of these pixels divided by the total number of pixels on the face of a stone are used to measure scintillation. The higher the number, the greater the scintillation value. Polish of the table is determined by extracting the average R.G.B. values from the table image A23. The average R.G.B. values are adjusted for the incident light. A polish grade for the table is assigned by comparing the adjusted R.G.B. values to a standard. Once the flaw, brilliance, scintillation, and polish analysis are completed a search is done of the database of analysis station 14 to determine the existence of a record which would indicate any prior analysis of the gemstone, or an indication whether the gemstone has been included in a lost or stolen record field of the database for matching. A hierarchical search technique is used to reduce search time considerably in steps 264 and 266. If more than one gemstone is identified by the search, comparison is made by the data processor to establish a perfect match. Ideally, only after the step is completed, a cluster or linear discriminant model is used to assign color based on tri-stimulus coordinates, weight of a diamond, flaws, and fluorescence in step 268. For newly cut diamonds, searching the database is obviously unnecessary. Results of analysis are saved and a report is printed or sent to the local station 8 which requested the analysis.

In addition to evaluating gemstones, the analysis station 14 matches the characteristics of the analyzed gemstones 7 to characteristic of gemstones previously analyzed by the apparatus 5 and stored in the database. Moreover, the database can be queried to inventory gemstones 7 possessing a certain characteristic and/or price range as the database maintains current market price information used in the appraisal of gemstones. The analysis station 14 can perform grading, matching, identification, sorting, and appraisal functions independently or in any specified combination and communicate these reports as a multimedia presentation to local terminals.

The terms and expressions which have been employed are used as terms of description and not of limitation. There is no intention in the use of such terms and expressions of excluding any equivalents of the features shown and described or portions thereof. It is recognized, however, that various modifications are possible within the scope of the invention as claimed.

What is claimed is:

1. Apparatus for grading and identification of a gemstone comprising:

a housing;

a platform mounted in said housing for supporting a gemstone;

lighting means disposed within said housing for illuminating the gemstone supported by said platform;

an electronic imaging device mounted in said housing and adapted for viewing the gemstone on said platform from each of a plurality of different viewing angles and for generating electronic image signals corresponding to a physical characteristic of the gemstone; and an electronic data processor operatively connected to said lighting means and said electronic imaging device, said electronic data processor being programmed with an instruction set for controlling said lighting means and said electronic imaging device, and for receiving and storing the electronic image signals.

2. Apparatus as set forth in claim 1, wherein said platform comprises means for rotating said platform about an axis that is common to said platform and the gemstone supported thereon.

3. Apparatus as set forth in claim 2, wherein said rotating means comprises means for incrementally rotating said platform about said axis.

4. Apparatus as set forth in claim 1, wherein the lighting means comprises a stationary light source.

5. Apparatus as set forth in claim 1 wherein said lighting means comprises:
   a first light source disposed at a first position relative to the gemstone; and
   a second light source disposed at a second position relative to the gemstone.

6. Apparatus as set forth in claim 1 wherein said electronic data processor is programmed for generating a data file containing information on the physical characteristic of the gemstone based on the electronic image signals and the electronic data processor comprises a data storage device for storing the data file for later retrieval.

7. Apparatus as set forth in claim 6 wherein the information in the data file is stored in a data format selected from the group consisting of textual data, video data, graphic data, audio data, or a combination thereof.

8. A method of analyzing incident and reflected light data for use in grading, testing, or identifying a gemstone, the method comprising the steps of:
   placing a gemstone on a platform within an area substantially free of light;
   positioning a light responsive element of an electronic imaging device so as to view the gemstone from different aspects thereof with said light responsive element;
   illuminating the gemstone from said different aspects thereof; and
   capturing incident light data from the different aspects of the gemstone with the electronic imaging device and storing the light data as an image data set in a data processor having a storage device.

9. The method set forth in claim 8 wherein the step of capturing the incident light data is performed without changing the focal length of the camera.

10. The method set forth in claim 8 further comprising the step of positioning the light responsive element relative to the gemstone so as to capture the incident light data without changing the focal length of the camera.

11. The method set forth in claim 8 comprising the step of incrementally rotating the platform to present the different aspects of the gemstone to said electronic imaging device.

12. The method set forth in claim 8 wherein the step of illuminating the gemstone comprises the step illuminating the gemstone with light containing a specific light frequency or a combination of light frequencies in the visible or invisible spectra.

13. The method set forth in claim 12 wherein the step of illuminating the gemstone comprises the step of illuminating the gemstone with ultraviolet light.

14. The method set forth in claim 13 further comprising the step of analyzing the light data to detect the presence of treatments or to distinguish a synthetic or simulant from a genuine gemstone.

15. The method set forth in claim 12 wherein the step of illuminating the gemstone comprises the step of illuminating the gemstone with light having a color rendition and an ultraviolet component that resembles North Daylight.

16. The method set forth in claim 8 comprising the step of analyzing the light data to measure the brilliance of the gemstone.

17. The method set forth in claim 16 wherein the step of analyzing the light data to measure the brilliance of the gemstone comprises the step of capturing the incident light data from a table side of the gemstone and determining an average of the total illumination over the face of the gemstone.

18. The method set forth in claim 17 comprising the step of adjusting for the intensity of the incident light on the gemstone.

19. The method set forth in claim 8 comprising the step of analyzing the light data to measure the scintillation of the gemstone.

20. The method set forth in claim 19 wherein the step of analyzing the light data to measure the scintillation of the gemstone comprises the steps of:
   generating a gray scale image of the gemstone;
   thresholding the gray scale image;
   measuring the number of image pixels having a gray level greater than a threshold gray level;
   measuring the number of image pixels in the area of the face of the gemstone; and then
   determining the ratio of the number of image pixels having a gray level greater than the threshold gray level to the number of image pixels in the area of the face of the gemstone.

21. A method for characterizing a gemstone comprising the steps of:
   viewing a gemstone with an electronic imaging device;
   generating electronic image signals corresponding to a plurality of different physical characteristics of the gemstone;
   controlling said electronic imaging device with a local data processor that is programmed with an instruction set for controlling said electronic imaging device to obtain the electronic image signals corresponding to the different physical characteristics of the gemstone;
   processing the electronic image signals from said electronic imaging device to provide a data file containing information about the different physical characteristics of the gemstone; and
   transmitting the data file to a central processing system that is located remotely from said local data processor.

22. The method set forth in claim 21 further comprising the steps of receiving the data file at the central processing system and processing the information in the data file at the central processing system to provide gemstone information selected from the group consisting of grading information, images, appraisal information, source of origin, physical identification, and combinations thereof, for the gemstone.

23. The method set forth in claim 22 further comprising the step of transmitting the gemstone information electronically to a remote terminal.

24. The method set forth in claim 21 further comprising the step of storing the grading information in a database of gemstone grading and identification information at said central processing system.

25. The method set forth in claim 21 further comprising the step of generating an appraisal report for the gemstone at the central processing system based on the information in the data file.

26. The method set forth in claim 25 comprising the step of storing the appraisal report in a database of gemstone grading and identification information at said central processing system.

27. The method set forth in claim 21 further comprising the steps of generating the instruction set for use by said local data processor and transmitting the instruction set from the central data processor to the local data processor.

28. The method set forth in claim 21 wherein the step of generating the electronic image signals comprises the steps of sequentially illuminating the gemstone with a light source or combination of light sources and capturing light that is reflected by or transmitted through the gemstone from each of said light sources or combination of light sources with the electronic imaging device.

29. The method set forth in claim 28 comprising the step of generating a pixel data set corresponding to the reflected or transmitted light captured by the electronic imaging device.

30. The method set forth in claim 21 wherein the information in the data file is stored in data format selected from the group consisting of textual data, video data, graphic data, audio data, or a combination thereof.

31. A method for characterizing a gemstone comprising the steps of:

receiving a data file containing information about different physical characteristics of a gemstone;

processing the information in the data file to provide grading information for the gemstone; and generating and appraisal report for the gemstone.

32. The method set forth in claim 31 comprising the step of storing the grading information and the appraisal report in a database of gemstone grading and identification information.

33. The method set forth in claim 32 wherein the information in the data file is stored in a data format selected from the group consisting of textual data, video data, graphic data, audio data, or a combination thereof.

34. The method set forth in claim 33 comprising the step of electronically transferring the information in the data file in connection with a transaction involving a gemstone.

35. The method set forth in claim 34 wherein the transition is selected from the group consisting of marketing of a gemstone, retail or wholesale purchasing or selling of a gemstone, or a combination thereof.

36. The method set forth in claim 31 comprising the steps of generating a data processor instruction set for use at a remote processing station and transmitting the instruction set to the remote processing station for installation on a local data processor at said remote processing station.

37. The method set forth in claim 36 wherein the step of generating the data processor instruction set comprises the step of generating a sequence of instructions executable by the local data processor for controlling an imaging device at said local processing station.

38. The method of claim 37 comprising the step of downloading the appraisal report to a local data processor at a remote processing station.

39. A method of analyzing a gemstone for flaws comprising the steps of:

providing a translucent plate that is formed to diffuse light passing therethrough;

applying an immersion fluid to the translucent plate;

placing a gemstone on said translucent plate such that it contacts the oil on said plate;

illuminating said gemstone with diffused light transmitted through said translucent plate;

capturing light data transmitting through said gemstone with an imaging device; and analyzing the light data to detect the presence of a flaw in said gemstone.

40. The method of claim 39 wherein the step of analyzing the light data comprises the steps of determining and recording the location of the flaw in said gemstone.

41. The method of claim 39 wherein the step of analyzing the light data further comprises the steps of measuring and recording the size of the flaw.

42. A method of analyzing a gemstone for flaws comprising the steps of:

providing a translucent vessel that is formed to diffuse light passing therethrough;

placing a gemstone on said translucent vessel;

immersing said gemstone in translucent immersion fluid;

illuminating said gemstone with light transmitted through said translucent vessel;

capturing light data transmitted through said gemstone; and analyzing the light data to detect the presence of a flow in said gemstone.

43. The method of claim 42 wherein the step of analyzing the light data comprises the steps of determining and recording the location of the flaw in said gemstone.

44. The method of claim 43 wherein the step of analyzing the light data further comprises the steps of measuring and recording the size of the flaw.

45. A method of grading a gemstone comprising the steps of:

compiling a database of physical characteristics for a plurality of known gemstones for each of the plurality of gemstones;

measuring a physical characteristic of an unknown gemstone;

analyzing the measured physical characteristic of the unknown gemstone relative to the database of gemstone characteristics; and assigning a grade to the gemstone for the measured characteristic.

46. The method set forth in claim 45 wherein the step of measuring a physical characteristic of the gemstone comprises the step of measuring a gemstone characteristic selected from the group consisting of color, cut, shape, size, brilliance, scintillation, polish, fluorescence, flaws, and combinations thereof.

47. The method set forth in claim 45 wherein the step of measuring a physical characteristic of the gemstone comprises the step of measuring a gemstone characteristic selected from the group consisting of table dimensions, number of facets, facet dimensions, girdle dimensions, and combinations thereof.

48. The method set forth in claim 47 further comprising the steps of comparing the measured physical characteristics of two or more gemstones and then matching or sorting the gemstones according to at least one measured characteristic thereof.

49. The method set forth in claim 45 wherein the measuring step comprises measuring a plurality of physical characteristics of the unknown gemstone; the analyzing step comprises analyzing the measured physical characteristics of the unknown gemstone using a multivariate analysis of the measured physical characteristics relative to the database of gemstone characteristics; and the assigning step comprises assigning a grade to the unknown gemstone based on the plurality of measured characteristics.

50. The method set forth in any of claims 45 to 49 further comprising the step of adding the measured physical characteristic of the unknown gemstone to the database.

51. The method set forth in claim 50 comprising the step of searching the database to select a gemstone based on one or more physical characteristics stored in the database.

52. The method set forth in any of claims 45 to 49 comprising the step of maintaining the database in a secure environment.

* * * * *

UNITED STATES PATENT AND TRADEMARK OFFICE
CERTIFICATE OF CORRECTION

PATENT NO. : 6,239,867 B1
DATED : May 29, 2001
INVENTOR(S) : Aggarwal

It is certified that error appears in the above-identified patent and that said Letters Patent is hereby corrected as shown below:

Column 1,
Line 61, "gain" should be -- gem --.

Column 7,
Line 2, "or" should be -- of --.

Column 9,
Line 20, "local" should be -- focal --.

Column 12,
Line 3, "actuator" should be -- actuation --;
Line 26, "therethrough, sliding" should be -- therethrough. Sliding --.

Column 14,
Line 9, "A" should be -- At --;
Line 50, "of" should be -- a --.

Claim 38,
Line 1, "claim 37" should be -- Claim 31 --.

Claim 42,
Line 11, "flow" should be -- flaw --.

Signed and Sealed this

Eighteenth Day of December, 2001

Attest:

Attesting Officer

JAMES E. ROGAN
Director of the United States Patent and Trademark Office